United States Patent [19]

Lamb

[11] Patent Number: 5,451,203
[45] Date of Patent: Sep. 19, 1995

[54] TRACTION MECHANISM

[75] Inventor: Steve Lamb, Union City, Calif.

[73] Assignee: Orthopedic Systems, Inc., Union City, Calif.

[21] Appl. No.: 282,803

[22] Filed: Jul. 29, 1994

[51] Int. Cl.⁶ .............................. A61F 5/00; A61F 2/08
[52] U.S. Cl. ........................................ 602/36; 128/880; 602/22; 602/63; 602/32; 623/13; 2/163
[58] Field of Search ................ 602/5, 21, 22, 32–36, 602/60–64; 482/47, 48; 623/13; 128/878–880; 2/159, 163

[56] References Cited

U.S. PATENT DOCUMENTS

| | | |
|---|---|---|
| 2,146,933 | 2/1939 | Budin . |
| 2,688,961 | 9/1954 | Thomas . |
| 3,693,617 | 9/1972 | Trott . |
| 3,850,166 | 11/1974 | Tamny et al. . |
| 3,872,861 | 3/1975 | Tamny et al. . |
| 4,604,821 | 8/1986 | Moser . |
| 4,679,548 | 7/1987 | Pecheux ........................ 602/22 X |
| 4,741,087 | 5/1988 | Plummer . |
| 4,775,380 | 10/1988 | Seedham et al. ............ 623/13 X |
| 4,917,699 | 4/1990 | Chervitz ........................ 623/13 |
| 4,966,167 | 10/1990 | Jacobs et al. ................. 182/849 |
| 5,027,802 | 7/1991 | Donohue . |
| 5,074,291 | 12/1991 | Carter . |
| 5,116,373 | 5/1992 | Jakob et al. ................... 623/13 |
| 5,191,903 | 3/1993 | Donohue . |

*Primary Examiner*—Linda C. M. Dvorak
*Attorney, Agent, or Firm*—Bielen, Peterson & Lampe

[57] ABSTRACT

A traction mechanism utilizing a tube of flexible material possessing an inner chamber which includes a dimension that is reducible in size upon the application of tension to the tube. Likewise, the tube chamber dimension is expandable in size upon the application of compression on the tube. The first end portion of the tube extends from a closure and terminates in a second open end portion. A tube may be formed of flexible material and possess a dual wall construction. A line extends from the first end portion of the tube to the second end portion thereof for attachment at that point. Pulling the line compresses the tube and thus increases the dimension of the same, releasing items held thereby in traction.

7 Claims, 2 Drawing Sheets

TRACTION MECHANISM

BACKGROUND OF THE INVENTION

The present invention relates to a novel and useful traction mechanism which is particularly applicable in the medical field.

Traction mechanisms have been used in orthopedic medicine to hold portions of the anatomy while performing medical procedures such as bone reduction, ligament suturing, and the like. U.S. Pat. No. 4,741,087 describes a braided sleeving material which is formed into a tube. U.S. Pat. Nos. 2,688,961, 3,693,617, 3,850,166, 3,872,861, and 5,074,291 describe hand traction devices employing "finger traps" having a mesh construction.

U.S. Pat. Nos. 2,146,933, 5,027,802, and 5,191,903 describe braided gripping tubes which are used to apply a traction force to fingers of the hand or toes of the foot.

To release the traction tube from an appendage, a pushing or spreading force is normally applied to the open end of the same. At times the open end of a traction tube is not readily accessible to release the digit, appendage, or other anatomical part after traction has occurred.

A mechanism which permits the user to achieve remote release of an anatomical appendage following traction would be a notable advance in the medical field.

SUMMARY OF THE INVENTION

In accordance with the present invention a novel and useful traction mechanism is herein provided.

The traction mechanism of the present application employs a tube of flexible material such as a mesh. The tube may include a dual wall construction such that two walls meet at the folded end at the open end portion of the tube. The tube itself is capable of being reducible in size upon the application of tension and expandable in size upon the application of compression. In this regard, the tube serves as a typical finger trap, although its use is not limited to fingers. For example, ligaments, tendons, and the like may also be drawn by the mechanism of the present invention. The tube is formed with a first end portion which is sealed by a closure and an open second end portion. The anatomical appendage, or the like is intended to be placed in the open second end portion of the tube. The application of tension to the tube causes the tube walls to hold such an object within the chamber of the tube by decreasing the width of the chamber.

A line is also employed in the present invention and extends from the first end portion of the tube to the second end portion thereof. A line increases a dimension of the inner chamber, preferably the width, of the tube upon the application of a pulling force or tension on the line in the vicinity of the first end portion of the tube. A line may be guided to the second end portion of the tube by the use of an appurtenant guide, weaving the line through the mesh construction of the tube, or simply directing the line between the walls of the tube when the tube is formed in a dual wall configuration. A line is connected to the tube in the vicinity of the open second end portion of the tube and directed to the first end portion of the tube for accessibility. The line may be formed into a loop at the second end portion of the tube such that both bitter ends of the line are connected and guided into spaced fixation at the second end portion of the tube. The closure circumscribing the first end portion the tube may also circumscribe the line to maintain its position relative to the tube and permit the loop portion of the line to extend from the first end portion of the tube for accessibility. Of course, the line is slidable or movable relative to the closure.

It may be apparent that a novel and useful traction mechanism has been described.

It is therefore an object of the present invention to provide a traction mechanism for anatomical appendages which may be employed in the performance of surgical procedures such as reduction of bone fractures.

Another object of the present invention is to provide a traction mechanism for an object such as an anatomical appendage which is easily used to apply traction to the appendage and includes a structure for releasing the same following traction.

Yet another object of the present invention is to provide a traction mechanism for an object which includes a structure for releasing traction on the object without contact of the object being held in traction.

A further object of the present invention is to provide a traction mechanism for a surgical procedure which is simple to manufacture and use during surgery.

Yet another object of the present invention is to provide a traction mechanism which is capable of pulling, locating, and releasing anatomical objects.

The invention possesses other objects and advantages especially as concerns particular characteristics and features thereof which will become apparent as the specification continues.

Figure 1:
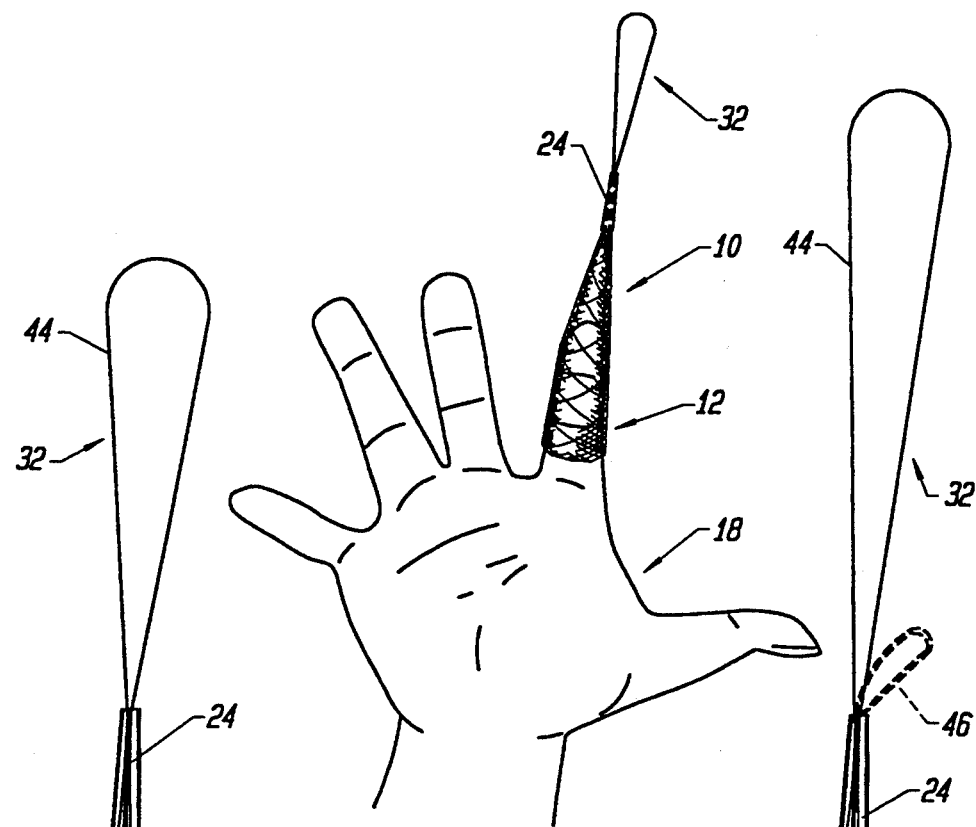
FIG. 1 is a front elevational view of the mechanism of the present invention in place on the index finger of a hand.

For a better understanding of the invention reference is made to the following detailed description of the preferred embodiments thereof which should be referenced to the prior described drawings.

DETAILED DESCRIPTION OF THE PREFERRED EMBODIMENTS

Various aspects of the present invention will evolve from the following detailed description of the preferred embodiments which should be taken in conjunction with the prior described drawings.

The invention as a whole is depicted in the drawings by reference character 10. The traction mechanism 10 includes as one of its elements a tube 12 formed of mesh material which is of flexible construction. For example, the mesh material of tube 12 may take the form of a polypropylene, nylon, or other plastic woven fabric. Tube 12 in its general form is known in the orthopedic field as a "finger trap", although tube 12 may be formed with an inner chamber 14 that is capable of encompassing and holding an anatomical appendage such as finger 16 of hand 18, a natural or artificial ligament, and the like. Tube 12 possesses a first end portion 20 and a second end portion 22. First end portion 20 is tapered and bunched by a closure 24 in the form of a cylindrical member which is heat shrunk about first end portion 20. Second end portion 22 is open to chamber 14. As depicted in the drawings, tube 12 includes an outer first wall 26 and an inner second wall 28 that are connected to one another at folded end 30. Thus, folded end 30 presents a smooth surface to finger 16. Second end portion of tube 12 at folded end 30 may possess a slight flare to permit entry of finger 16 into chamber 14 in this regard. Since tube 12 is flexible, the width dimension of the same may change depending on the application of tension on the same, which will be hereinafter described in detail.

Line 32 is also found in the present invention. Line 32 extends from the vicinity of first end portion 20 of tube 12 to second end portion 22 of tube 12. Bitter ends 34 and 36 of line 32 are passed through the space 38 between walls 26 and 28. Tips 40 and 42 are fixed to tube 12 in opposition to one another at second portion 22 by knotting, sonic welding, gluing, or the like. Line 32 also extends out of tube 12 at first end portion thereof. Line 32 forms a loop 44 which is easily grasped by the fingers of the user of mechanism 10. It should be noted that closure 24 encompasses line 32 and permits loop 44 to extend therefrom. Line 32 is also allowed to move or slide relative to closure 24.

Figure 2:
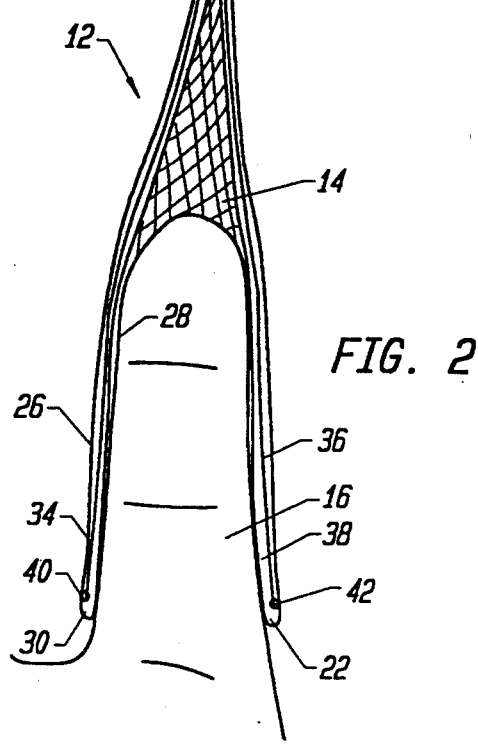
FIG. 2 is a sectional view of the mechanism of the present invention on the index finger of the hand in traction.
Figure 3:
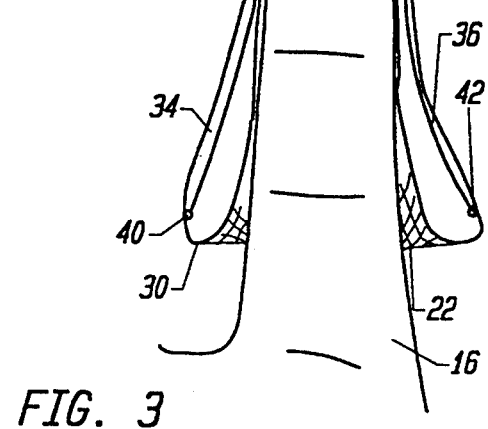
FIG. 3 is a sectional view of the mechanism of the present invention being released from traction on the index finger of the hand.
Figure 4:
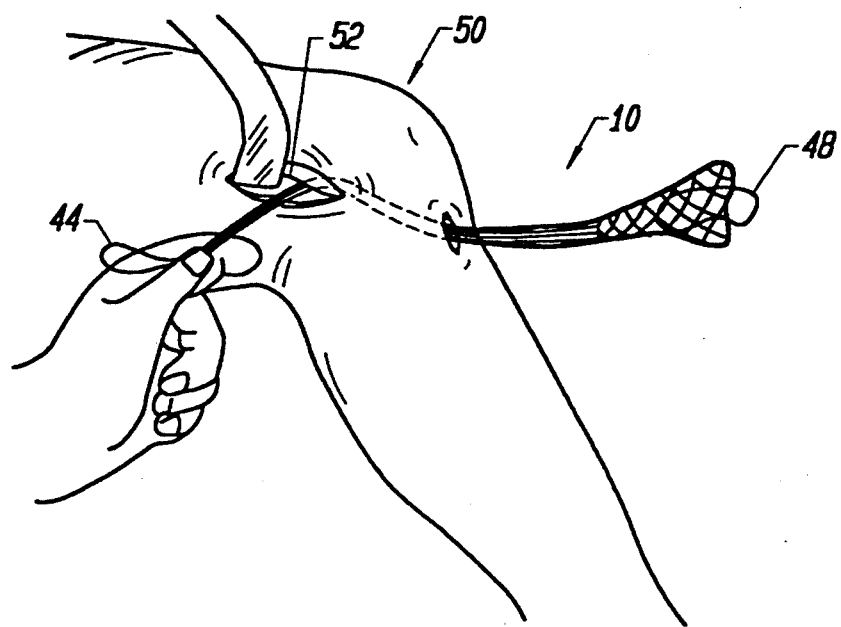
FIG. 4 is a front elevational view of the mechanism of the present invention employed in meniscus implantations.

In operation, FIG. 1, the user places open second end portion 22 of tube 12 over an appendage such as finger 16. Upon the application of tension normally applied by pulling at first end portion 20 of tube 12, the dimension of chamber 14 decreases in cross section. In other words, the width dimension of tube 12 decreases and the length of tube 12 increases, FIGS. 2 and 3. Thus, tube 12 acts as a normal finger trap. To release the finger trap, the user pulls on loop 44 of line 32. Bitter ends 34 and 36 of line 32 compresses the length of tube 12 and increases the width of the same at second end portion 22. This increase in width dimension near folded end 30 essentially releases the holding force on finger 16. It should be noted that line 32 is permitted to slide through closure 24 in this regard. A ring 46 may also be placed within closure 24 to permit alternate means of holding tube 12. It should be noted that although a finger 16 is used as an example in the preferred embodiments, mechanism 10 may be employed to tension and release other appendages such as toes, meniscuses, and the like, without contacting the appendage or applying force to second end portion 22 of tube 12. For example, FIG. 4 shows mechanism 10 being used as a traction device for implantation of prosthetic meniscus 48 in knee 50. Again, when prosthetic meniscus is placed within knee 50 for surgical attachment, loop 44 would be tensioned to release meniscus 48. Mechanism 10 would then be pulled from surgical wound 52.

While in the foregoing, embodiments of the present invention have been set forth in considerable detail for the purposes of making a complete disclosure of the invention, it may be apparent to those of skill in the art that numerous changes may be made in such details without departing from the spirit and principles of the invention.

What is claimed is:

1. A traction mechanism for an object comprising:
   a. a tube of flexible material having an inner chamber, said tube possessing a dimension being reducible in size upon the application of tension thereon, said tube dimension being expandable in size upon the application of compression thereon, said tube including a first end portion and a second end portion, said second end portion capable of holding an object;
   b. a line independently formed from said tube, said line extending from said first end portion to said second end portion of said tube said line applies compression to the second end of the tube thereby increasing said size of said inner chamber of said tube upon the application of tension on said line in the vicinity of said first end portion of said tube.

2. The traction mechanism of claim 1 in which said tube of flexible material includes one wall of mesh.

3. The traction mechanism of claim 2 which additionally includes another wall, said another wall being connected to said one wall to form a folded end at said second end portion of said tube.

4. The traction mechanism of claim 3 in which said line includes a first end portion connected to said second end portion of said tube, and a second end portion connected to said second end portion of said tube, said line extending outside said tube at said first end portion of said tube and extending between said one and another walls.

5. The traction mechanism of claim 4 in which said line forms a loop at the extension of said line outside said first end portion of said tube.

6. The traction mechanism of claim 1 which additionally comprises a closure of said first end portion of said tube, said closure at least partially circumscribing said first end portion of said tube and said line.

7. The traction mechanism of claim 6 in which said closure circumscribing said line, permits movement of said line relative to said closure.

* * * * *